United States Patent
Erdmann et al.

(10) Patent No.: US 6,902,608 B2
(45) Date of Patent: Jun. 7, 2005

(54) DENTAL MATERIAL CONTAINING PHOSPHONIC ACIDS

(75) Inventors: Christoph Erdmann, Hamburg (DE); Silke Ziegler, Hamburg (DE); Stephan Neffgen, Hamburg (DE); Carsten Bolln, Schenefeld (DE); Wolfgang Mühlbauer, Hamburg (DE); Rainer Lück, Tornesch (DE)

(73) Assignee: Ernst Muhlbauer GmbH & Co., KG (DE)

( * ) Notice: Subject to any disclaimer, the term of this patent is extended or adjusted under 35 U.S.C. 154(b) by 0 days.

(21) Appl. No.: 10/332,344

(22) PCT Filed: Jul. 3, 2001

(86) PCT No.: PCT/EP01/07602

§ 371 (c)(1),
(2), (4) Date: Jan. 6, 2003

(87) PCT Pub. No.: WO02/02057

PCT Pub. Date: Jan. 10, 2002

(65) Prior Publication Data

US 2003/0167968 A1 Sep. 11, 2003

(51) Int. Cl.$^7$ ................................................ A61K 6/083
(52) U.S. Cl. .......................... 106/35; 523/116; 433/226; 433/228.1
(58) Field of Search .......................... 106/35; 523/116; 433/226, 228.1

(56) References Cited

U.S. PATENT DOCUMENTS

| | | | | | |
|---|---|---|---|---|---|
| 4,272,512 | A | * | 6/1981 | Gaffar | 424/49 |
| 4,526,728 | A | * | 7/1985 | Finke et al. | 562/15 |
| 4,650,847 | A | * | 3/1987 | Omura et al. | 526/276 |
| 5,321,053 | A | * | 6/1994 | Hino et al. | 522/26 |
| 6,172,131 | B1 | * | 1/2001 | Moszner et al. | 523/116 |

FOREIGN PATENT DOCUMENTS

| | | | |
|---|---|---|---|
| DE | DD 273846 | * | 11/1989 |
| DE | 199 18 974 | | 12/1999 |
| EP | 0 089 654 | | 9/1983 |
| EP | 0 909 761 | | 4/1999 |

OTHER PUBLICATIONS

Ignatius et al. "Novel Carbamoyl Phosphate Monomers and polymers from unsaturated isocyanates," *Journal of Polymer Science*, 31:239–247 (Jan. 1993).

* cited by examiner

Primary Examiner—C. Melissa Koslow
(74) Attorney, Agent, or Firm—Medlen & Carroll, LLP

(57) ABSTRACT

The invention relates to dental materials which contain hydrolysis-resistant phosphonic acids with ethylenically unsaturated double bonds and which are especially suitable for use as adhesion promoters.

13 Claims, No Drawings

DENTAL MATERIAL CONTAINING PHOSPHONIC ACIDS

The invention relates to dental materials, in particular adhesion promoters or polymerizable cements, for example compomers or glass ionomer cements with polymerizable acids, which are known in principle from DE-A-3536076 and DE-A-3536077.

Dental materials with polymerizable phosphoric acids as comonomers are known; they usually comprise phosphoric acid and acrylates or methacrylates. For example, DE-A-19647140 discloses the esterification of a hydroxyalkyl acrylate or methacrylate with phosphate. A disadvantage of these substances is that they have a low resistance to hydrolysis, since the ester bonds between phosphate and alkyl chain and between methacrylate and alkyl chain can be easily cleaved hydrolytically. This reduces the storage stability of the dental material and results, under the conditions in the oral cavity, in a reduced durability in the tooth.

DE-A-19746708 discloses the bonding of phosphonates to the methyl group of a methacrylate ester via a spacer. Phosphine oxides linked to methacrylates or styrene via a urethane group are also known (J. Smid et al., Journal of Polymer Science, Part A Polymer Chemistry, 31, 239–247 (1993)), as is the linking of phosphonic acids to methacrylates via an ester (DE-A-19918974). The invention is based on the object of preparing dental materials of the kind mentioned at the start which have good adhesive properties and a high resistance to hydrolysis.

The invention achieves this object through the characteristics of the main claim. Accordingly, the dental materials comprise phosphonic acids with the structure given below or salts of these acids:

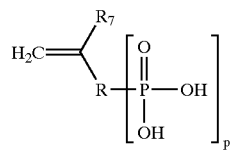

in which R, $R_7$ and p are, independently of one another: either:
  a) R: alkyl group or alkylene group with at least 6 C-atoms or aryl group,
     $R_7$: H, methyl, ethyl, propyl, isopropyl or butyl,
     p is 1 or 2;
  or:
  b) R: —CO—$NR_1$—$R_8$—
     with $R_1$ equal to H, alkyl or aryl,
     with $R_8$ equal to aryl or $C_nH_{2n}$
     in which $4 \leq n \leq 18$,
     or $R_8$ is $C_nH_{2n}$—$Si(R_5)_2$—[O—$Si(R_5)_2]_m$—$C_nH_{2n}$
     in which $3 \leq n \leq 12$,
       $1 \leq m \leq 10$, and
       $R_5$ is methyl, ethyl or phenyl,
     or $R_8$ is $C_nH_{2n}$—COONH—$C_nH_{2n}$
     in which $4 \leq n \leq 12$, and in which $R_8$ can have ether or additional urethane groups,
     $R_7$ and p are defined as in a);
  or:
  c) R:

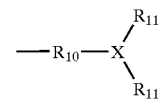

with $R_{10}$ chosen from the group consisting of aryl groups, alkyl groups with at least 3 C-atoms or polyether groups with 1 to 10 polyether units and with $R_{11}$ chosen, identically or differently, from the group consisting of alkyl groups and aryl groups,
  with X equal to N, B or CH,
  $R_7$: $COOR_9$, $CONHR_9$, H or phenyl with $R_9$ chosen from the group consisting of methyl, ethyl, propyl, isopropyl and butyl,
  p is equal to 2.

The invention is based on the surprising discovery that molecules with a relatively long chain bridge between phosphonic acid group and reactive double bond, as defined in the claim, have a high resistance to hydrolysis and, at the same time, improved adhesive properties.

Preferred embodiments of the invention are given in the subclaims.

A preferred embodiment of the invention has the structure given below:

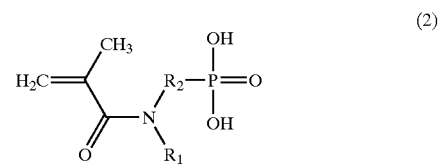

(2)

$R_1$ is hydrogen or an alkyl or aryl group. Preferably, $R_1$ is chosen from the group consisting of hydrogen, methyl, ethyl and isopropyl. $R_2$ is an alkyl group with 4 to 18 C-atoms which can be straight or branched. Preferably, it comprises 6 to 12 C-atoms. In the context of the invention, $R_2$ can also have the form of an alkyl chain interrupted by ether groups or additional urethane groups.

In an additional preferred embodiment, the phosphonic acids have the following structure:

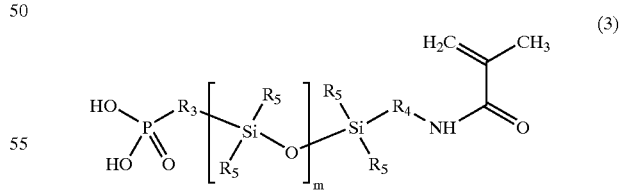

(3)

In this formula, $R_3$ or $R_4$ are aryl or alkyl groups. The alkyl groups can be straight or branched and preferably have 3 to 12 C-atoms. The substituents $R_5$ are identical or different and are methyl, ethyl or phenyl groups. m is 1 to 10.

Among the phosphonic acids with silicone components in the bridging compound between reactive double bond and phosphonic acid, the following structure is preferred:

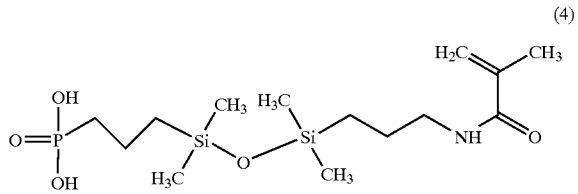
(4)

The following diphosphonates can preferably be used in the dental materials according to the invention:

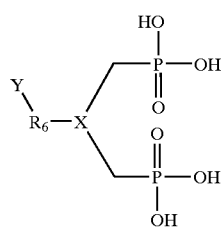
(5)

X is nitrogen, boron or a CH group, $R_6$ is a straight or branched alkyl group with at least 3 C-atoms, an aryl group or a polyether group with 1 to 10 polyether units, and Y comprises ethylenically unsaturated double bonds; Y is in particular chosen from the group consisting of $CH_2=CH—O—$, styrene, methacrylamide and $CH_2=C(COOR_{12})—CH_2—$, in which $R_{12}$ is H, methyl, ethyl, propyl, isopropyl or butyl.

The invention also relates to the use of a dental material according to the invention as adhesion promoter, compomer or polymerizable cement.

When used as adhesion promoter, the dental material can consist exclusively of the phosphonic acids mentioned or of their salts; it can comprise one or more solvents and/or additional polymerizable monomers, such as, in particular, acrylates or methacrylates.

Suitable solvents for dental materials are familiar to a person skilled in the art; water, methanol, ethanol, isopropanol, acetone, ethyl methyl ketone, ethyl acetate and mixtures of the aforementioned compounds are preferred.

An addition of water-soluble methacrylates, for example hydroxyethyl (meth)acrylates or hydroxypropyl (meth)acrylates, is preferred. (Meth)acrylates having at least two methacrylate groups, for example ethylene glycol di(meth)acrylate, diethylene glycol di(meth)acrylate, triethylene glycol di(meth)acrylate, tetraethylene glycol di(meth)acrylate, hexanediol di(meth)acrylate, butanediol di(meth)acrylate, dodecanediol di(meth)acrylate, 2,2-bis[p-(hydroxy(meth)acryloyloxy)-phenyl]propane, ethoxylated bisphenol A di(meth)acrylate, glycerol di(meth)acrylate, urethane di(meth)acrylate, polyester urethane di(meth)acrylate, trimethylolpropane tri(meth)acrylate or dipentaerythritol penta(meth)acrylate, are preferably suitable as additional (meth) acrylates.

An additional acid in the form of a polymerizable carboxylic acid can also be added. Examples which may be mentioned are mono(2-methacryloyloxyethyl)maleate, mono(2-methacryloyloxyethyl)phthalate and mono(2-methacryloyloxyethyl)trimellitate.

In the context of the invention, the term "dental materials" is understood to mean all materials which find application in the context of restorative or prosthetic work on teeth and which comprise phosphonates according to the invention or their salts. In a particularly advantageous way, the phosphonic acids according to the invention can be used in adhesion promoters.

Dental materials according to the invention can in particular have the following components:

2.5 to 60% by weight of phosphonic acids according to the invention or of their salts, 5 to 80% by weight of additional radically polymerizable comonomers, 0 to 80% by weight of solvents, 0 to 2% by weight of radical polymerization initiators, 0 to 80% by weight of fillers (depending on the intended application as adhesion promoter, cement or compomer).

A proportion of 0–20% by weight of fillers is preferred for adhesion promoters; cements and compomers are preferably solvent-free and the proportion of filler is preferably between 40 and 80% by weight.

The invention is described below using implementational examples. First the sometimes multistage synthesis of phosphonic acids according to the invention is described and subsequently the composition of implementational examples of adhesion promoters according to the invention is described.

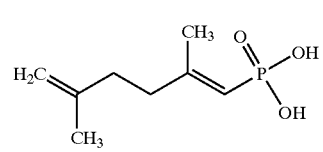
(6)

Synthesis of 1-(2,5-dimethyl-1,5-hexadienyl) phosphonic Acid (Formula (6))

104 g (0.5 mol) of $PCl_5$ are suspended in 1 l of toluene and 120 ml (0.6 mol) of 2,5-dimethyl-1,5-hexadiene are added dropwise with cooling. The reaction is maintained at 15° C. for 3 h more and $SO_2$ is then introduced over 3 h at 15° C. Toluene and $SOCl_2$ are then distilled off, 0.5 g of triphenylphosphine is added and the mixture is maintained at 180° C. for 8 h under a slight vacuum.

The mixture is diluted with 100 ml of dichloromethane, and 300 ml of a 5M NaOH solution are added dropwise with cooling and vigorous stirring. After 2 h, the reaction mixture is diluted with 300 ml of water, and 300 ml of 25% phosphoric acid are added with cooling.

This mixture is extracted three times with 500 ml of dichloromethane, the organic phase is dried over $MgSO_4$ and the solvent is removed under vacuum. 42 g of a brown syrup are produced.

Yield: 44%

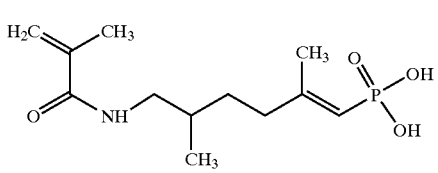
(7)

Synthesis of 6-methacrylamido-2,5-dimethyl-1-hexenylphosphonic Acid (Formula (7))

19 g of 1-(2,5-dimethyl-1,5-hexadienyl)phosphonic acid (0.1 mol) are dissolved in 100 ml of glacial acetic acid, and 60 mg of phenothiazine and 7 g (0.1 mol) of methacrylonitrile are added. 12 g of 85% sulfuric acid are added with cooling. After 24 h at 50° C., the preparation is cooled, 200 ml of water and 200 ml of dichloromethane are added and a total of three extractions with 200 ml of dichloromethane are carried out. The combined organic phases are extracted a further two times with water and then dried over a molecular sieve.

Yield: 18 g (66%)

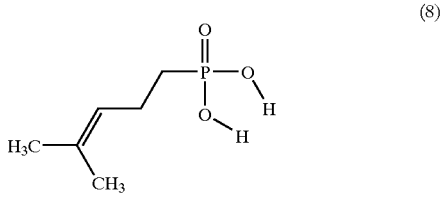

(8)

Synthesis of 1-(4-methyl-3-pentenyl)phosphonic Acid (Formula (8))

4 g of 1-bromo-4-methyl-3-pentene (48 mmol) are heated at 120° C. under nitrogen for 6 h with 7.5 g (60 mmol) of $P(OCH_3)_3$. The solution is then brought to ambient temperature, 35 ml of 37% hydrochloric acid are added and the solution is again heated at 100° C. for 20 h. The solution is then again cooled down and 10 ml of water are added. The aqueous phase is isolated and a light brownish precipitate is formed, which is dried in air.

Yield: 5.6 g 71%

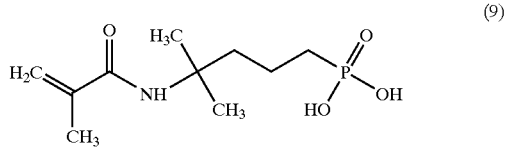

(9)

Synthesis of 4-methacrylamido-4-methylpentylphosphonic Acid (Formula (9))

1.9 g of 1-(4-methyl-4-pentenyl)phosphonic acid (12) (10 mmol) are dissolved in 10 ml of glacial acetic acid, and 6 mg of phenothiazine and 0.7 g (10 mmol) of methacrylonitrile are added. 1.2 g of 85% sulfuric acid are added with cooling. After 24 h at 50° C., the preparation is cooled, 20 ml of water and 20 ml of dichloromethane are added and a total of three extractions with 20 ml of dichloromethane are carried out. The combined organic phases are extracted a further two times with water and then dried over a molecular sieve.

Yield: 1.3 g (52%)

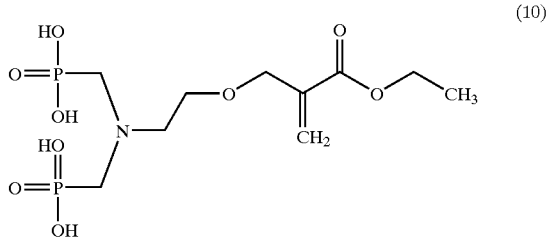

(10)

Synthesis of 2-(ethyloxycarbonyl)-2-propenyl-1-oxyethylaminobismethylenephosphonic Acid (Formula (10))

4.45 g (60 mmol) of KOH are stirred in 50 ml of DMSO for five minutes at ambient temperature. 2.49 g (10 mmol) of ethanolamino-N,N-bismethylenephosphonic acid are then carefully added. 2.94 g (15 mmol) of ethyl α-bromomethylacrylate are slowly added dropwise to the weakly colored suspension. The reaction preparation is stirred at ambient temperature for 24 h, 50 ml of cold water are subsequently added, the pH is adjusted to an acidic value, extraction is carried out with 50 ml of dichloromethane, the organic phase is dried and the solvent is removed under vacuum. The remaining waxy residue is dried in a drying cupboard.

Yield: 1.5 g (40%)

Alternative Possibility for the Synthesis of 4-methacrylamido-4-methylpentylphosphonic Acid (Formula (9))

1-(4-Methyl-4-pentenyl)phosphonic Acid (Formula (8))
Diethyl 1-(4-methyl-4-pentenyl)phosphonate 10 ml (0.0752 mol) of 5-bromo-2-methyl-2-pentene are heated at 160–190° C. with 15 ml (0.0856 mol) of $P(OC_2H_5)$, while distilling off the ethyl bromide being produced. The crude product is used further.

1-(4-Methyl-4-pentenyl)phosphonic Acid (Formula (8))

4 g (0.0182 mol) of diethyl 1-(4-methyl-4-pentenyl) phosphonate were dissolved in 40 ml of dried chloroform, 4 ml (0.04 mol) of trimethylsilyl bromide were added and the mixture was stirred at ambient temperature for 2 h. It was subsequently concentrated under vacuum, 40 ml of ethanol/water (1:1) were added and the mixture was likewise stirred for 2 h. It was then concentrated on a rotary evaporator and the residue was dried under vacuum with $P_2O_5$.

4-Methacrylamido-4-methylpentylphosphonic Acid (Formula (9))

3 mg of BHT and 1.53 ml (1.22 g; 0.0182 mol) of methacrylonitrile are added to 2.99 g of 1-(4-methyl-4-pentenyl)phosphonic acid (0.0182 mol). A mixture of 1 ml (1.84 g of 97%) sulfuric acid and 0.32 ml of water is then added dropwise at 20° C. After 16 h at 20–30° C., the temperature is raised within 4 h to 60° C. and this temperature is maintained for a further 16 h. The preparation is cooled down and is then dissolved in a mixture of 1.16 ml of water and 10 ml of methanol, and the sulfuric acid is neutralized through addition of a solution of 1.46 g of NaOH, 1.1 ml of water and 10 ml of methanol. However, the mixture must at the end still retain an acidic pH. The sodium sulfate is filtered off and the filtrate is fully concentrated under vacuum.

The compositions of three adhesion promoters according to the invention are shown in the following table (examples 1–3)

|  | Example 1 | Example 2 | Example 3 |
| --- | --- | --- | --- |
| Phosphonate | 10 g formula (7) | 1 g formula (9) | 1 g formula (10) |
| $H_2O$ | 5 g | 1 g | 1.5 g |
| Ethanol | 20 g | 4.5 g | 10 g |
| Bis-GMA* | 25 g | 0.75 g | 1 g |
| TEDMA** | 25 g | 1.25 g | 5 g |
| HEMA*** | 15 g | 1.5 g | 1.5 g |
| Ethyl dimethyl-aminobenzoate | 0.15 g | 0.018 g | 0.018 g |
| Camphorquinone | 0.1 g | 0.014 g | 0.014 g |

*2,2-Bis-[4-(2-hydroxy-3-methacryloyloxypropyl)phenyl]propane
**Triethylene glycol dimethacrylate
***2-Hydroxyethyl methacrylate

EXAMPLE 4

Two-component Adhesion Promoter System

The composition of an adhesion promoter system, consisting of a primer, which as active substance comprises one of the adhesion monomers according to the invention, and a bond, which in a second step is applied to a dental hard substance, provided beforehand with primer, is compiled below:

Component 1: Primer

| Substance | Proportion/% by weight |
|---|---|
| 4-Methacrylamido-4-methylpentyl-phosphonic acid (formula (9)) | 40.000 |
| Water | 28.875 |
| Ethanol | 28.875 |
| Camphorquinone | 0.800 |
| 2-Ethylhexyl 4-(dimethylamino)benzoate | 1.400 |
| 2,6-Di(tert-butyl)-4-methylphenol | 0.050 |

The individual substances of the primer are weighed out in a glass vessel and are mixed at ambient temperature with stirring until a homogeneous solution is produced.

Component 2: Bond

The commercially available Primer B of the adhesion promoter system Ecusit—Primer/Mono (Dental Material Gesellschaft mbH—Hamburg, Germany) is useful as bond.

EXAMPLE 5

Single-component Adhesion Promoter System

The composition of an adhesion promoter system, consisting of a component which comprises, inter alia, one of the adhesion monomers according to the invention, is compiled in the table below.

| Substance | Proportion/% by weight |
|---|---|
| 4-Methacrylamido-4-methylpentyl-phosphonic acid (formula (9)) | 10.00 |
| Water | 10.00 |
| Ethanol | 44.28 |
| Glycerin-1,3-dimethacrylate | 10.97 |
| Hydroxyethyl methacrylate | 15.00 |
| Bis-GMA | 7.50 |
| Camphorquinone | 0.80 |
| 2-Ethylhexyl 4-(dimethylamino)benzoate | 1.40 |
| 2,6-Di(tert-butyl)-4-methylphenol | 0.05 |

The individual substances of the adhesion promoter are weighed out in each case in a glass vessel and are mixed at ambient temperature with stirring until a homogeneous solution is produced.

EXAMPLE 6 (COMPARATIVE EXAMPLE)

The bond from example 4 (Primer B of the Ecusit Primer/Mono adhesion promoter system, Dental Material Gesellschaft, Hamburg, Germany) is used without prior application of the primer from example 4.

Shear Bond Strength Measurement:

A shear bond test is carried out to measure the adhesion of composites to dental hard substance when using the adhesion promoters according to the invention. For this, cattle incisors, from which the pulp has been removed beforehand and which in addition have been stored in 0.5% by weight chloramine T solution in water, are ground down under wet conditions on the front down to the dentin and are subsequently sanded flat under wet conditions with a fine sandpaper (P500). After storing for a short time in demineralized water, the sanded surface is blown dry and the adhesion promoter system is applied.

Two-component Adhesion Promoter (Example 4)

The primer from example 4 is rubbed into the sanded dentin surface with a microbrush for 20 s. Subsequently, the bond from example 4 is analogously applied, the surface is blown and is exposed to a dental lamp (Translux EC, Fa. Kulzer & Co GmbH, Wehrheim, Germany) for 20 s. A two-part Teflon mold with a cavity with a diameter of 3.0 mm is assembled, filled with a dental composite (Ecusit, Dental Material Gesellschaft mbH, Hamburg, Germany) and exposed for 40 s (Kulzer Translux EC).

Single-component Adhesion Promoter (Example 5)

The adhesion promoter from example 5 is rubbed into the sanded dentin surface with a microbrush for 20 s. Subsequently, the surface is blown and exposed to a dental lamp (Translux EC, Fa. Kulzer & Co GmbH, Wehrheim, Germany) for 20 s. The adhesion promoter from example 5 is again rubbed into the dentin surface with a microbrush for 20 s, the surface is blown and exposed to a dental lamp (Translux EC, Fa. Kulzer & Co GmbH, Wehrheim, Germany) for 20 s. A two-part Teflon mold with a cavity with a diameter of 3.0 mm is assembled, filled with a dental composite (Ecusit, Dental Material Gesellschaft mbH, Hamburg, Germany) and exposed for 40 s (Kulzer Translux EC).

Comparative Example (Example 6)

The bond from example 6 is rubbed into the sanded dentin surface with a microbrush for 20 s, blown with compressed air and exposed to a dental lamp (Translux EC, Fa. Kulzer & Co GmbH, Wehrheim, Germany) for 20 s. A two-part Teflon mold with a cavity with a diameter of 3.0 mm is assembled, filled with a dental composite (Ecusit, Dental Material Gesellschaft mbH, Hamburg, Germany) and exposed for 40 s (Kulzer Translux EC).

The Teflon mold is in each case removed and the preparation is stored in water, first at 37° C. for 23 h and then at 23° C. for 1 h. The preparation is subsequently inserted into a mounting for measurement of the shear bond strength (see ISO/DTS Committee Draft 11405, Ref. No. ISO/TC 106/SC 1 N 321 and the literature cited therein) and measured in an apparatus for determination of a force-displacement diagram (Z010, Zwick GmbH & Co, Ulm, Germany) at an advance rate of 0.50 mm/min. The test is carried out on several preparations (number n).

The results of the investigations are summarized in the table below:

| Example | n | Shear bond strength Mean value [MPa] |
|---|---|---|
| 4 | 10 | 17 |
| 5 | 3 | 9 |
| 6 | 10 | 0[1] |

[1]Composite test specimens become detached without resistance from the dentin surface.

What is claimed is:

1. A dental material, characterized in that it comprises one or more phosphonic acids with the following structure and/or salts of these acids:

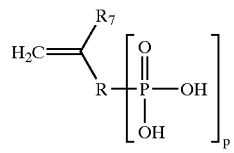

in which R, $R_7$ and p are, independently of one another: either:

a) R: alkyl group or alkylene group with at least 6 C-atoms or aryl group,
$R_7$: H, methyl, ethyl, propyl, isopropyl or butyl,
p is 1 or 2; or:

b) R: —CO—$NR_1$—$R_8$—
with $R_1$ equal to H, alkyl or aryl,
with $R_8$ equal to an alkylene group or a branched alkyl group with 4 to 18 C-atoms
or $R_8$ is $C_nH_{2n}$—$Si(R_5)_2$—[O—$Si(R_5)_2$]$_m$—$C_nH_{2n}$ in which $3 \leq n \leq 12$, $1 \leq m \leq 10$, and
$R_5$ is methyl, ethyl or phenyl,
or $R_8$ is $C_nH_{2n}$—COONH—$C_nH_{2n}$ in which $4 \leq n \leq 12$, and in which $R_8$ can have ether or additional urethane groups,
$R_7$: H, methyl, ethyl, propyl, isopropyl, or butyl,
p is 1 or 2; or:

c) R:

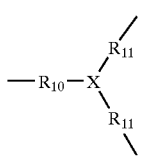

with $R_{10}$, chosen from the group consisting of aryl groups, alkyl groups with at least 3 C-atoms or polyether groups with 1 to 10 polyether units and with $R_{11}$ chosen, identically or differently, from the group consisting of alkyl groups and aryl groups, with X equal to N, B or CH,
$R_7$: $COOR_9$, $CONHR_9$, H or phenyl with $R_9$ chosen from the group consisting of methyl, ethyl, propyl, isopropyl and butyl,
p is equal to 2.

2. The dental material as claimed in claim 1, characterized in that the phosphonic acids have the following structure:

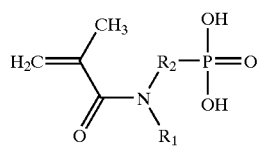

in which $R_2$ is an alkylene group or a branched alkyl group with 4 to 18 C-atoms, and $R_1$ is alkyl, aryl or H.

3. The dental material, characterized in that it comprises one or more phosphonic acids with the following structure and/or salts of these acids:

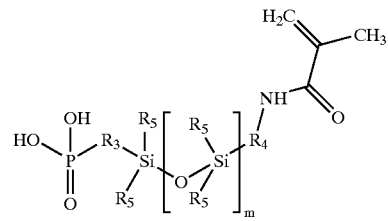

in which $R_3$ and $R_4$, which are identical or different, are aryl or alkyl having from 3 to 12 C-atoms; and substituents $R_5$, which are identical or different, are methyl, ethyl or phenyl, and m is 1 to 10.

4. A dental material, characterized in that it comprises one or more phosphonic acids with the following structure and/or salts of these acids:

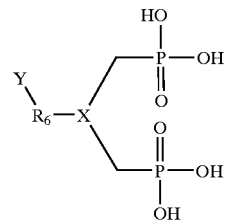

in which:
X is N, B or CH, and
$R_6$ is a straight or branched alkyl group with at least 3 C-atoms, an aryl group or a polyether group with 1 to 10 polyether units, and Y comprises ethylenically unsaturated double bonds.

5. The dental material as claimed in one of claims 1 to 4, characterized in that it additionally comprises solvents.

6. The dental material as claimed in claim 5, characterized in that the solvent is chosen from the group consisting of water, ethanol, methanol, isopropanol, acetone, ethyl methyl ketone and ethyl acetate.

7. The dental material as claimed in one of claims 1 to 4, characterized in that it comprises salts of the phosphonic acids.

8. The dental material as claimed in one of claims 1 to 4, characterized in that it additionally comprises acrylates or methacrylates.

9. The dental material as claimed in one of claims 1 to 4, characterized in that it additionally comprises fillers.

10. The dental material as claimed in one of claims 1 to 4, characterized in that it additionally comprises polymerization initiators.

11. An adhesion promoter comprising the dental material as claimed in claim 9, wherein said fillers comprise less than 20% by weight.

12. A compomer or polymerizable cement comprising the dental material as claimed in claim 9, wherein said fillers comprise between 40 and 80% by weight.

13. The dental material as claimed in claim 4, wherein Y is chosen from the group consisting of $CH_2$=CH—O—, styrene, methacrylamide, and $CH_2$=C($COOR_{12}$)—$CH_2$—, in which $R_{12}$ is H, methyl, ethyl, propyl, isopropyl or butyl.

* * * * *